(12) United States Patent
Takeda et al.

(10) Patent No.: US 7,732,218 B2
(45) Date of Patent: Jun. 8, 2010

(54) METHOD FOR PREPARING ANALYTICAL STANDARD, AND ANALYTICAL STANDARD PREPARED BY THE SAME

(75) Inventors: Shino Takeda, Chiba (JP); Masae Yukawa, Chiba (JP); Yoshikazu Nishimura, Chiba (JP)

(73) Assignee: National Institute of Radiological Sciences, Inage-Ku, Chiba (JP)

( * ) Notice: Subject to any disclaimer, the term of this patent is extended or adjusted under 35 U.S.C. 154(b) by 117 days.

(21) Appl. No.: 11/905,605

(22) Filed: Oct. 2, 2007

(65) Prior Publication Data

US 2009/0001323 A1 Jan. 1, 2009

(30) Foreign Application Priority Data

Oct. 3, 2006 (JP) .............................. 2006-271419

(51) Int. Cl.
*G01N 1/00* (2006.01)
*G01N 1/28* (2006.01)
(52) U.S. Cl. .............................. 436/174; 436/8; 436/77; 436/164; 436/166; 436/181; 436/183; 252/408.1
(58) Field of Classification Search ...................... 436/8, 436/73, 77, 81, 164, 166, 174, 181, 182, 436/183; 435/40.5, 40.52; 252/408.1
See application file for complete search history.

(56) References Cited

U.S. PATENT DOCUMENTS 5,981,292 A * 11/1999 Obenauf, Jr. ................. 436/175

6,221,987 B1 * 4/2001 Sugiyama .................... 526/231
2008/0310588 A1 * 12/2008 Cooper et al. ................. 378/45

OTHER PUBLICATIONS

Cholewa et al. Fresenius Zeitschrift Analytical Chemistry, vol. 326(7), pp. 742-743, 1987.*
Watanabe et al., "New method for quantitative mapping of metallic elements in tissue sections by electron probe microanalyser with wavelength dispersive spectrometers", Japanese Society of Electron Microscopy, Journal of Electron Microscopy, vol. 50, No. 1, 2001, pp. 77-82.
Watanabe et al., "Atomic-level detection by X-ray microanalysis in the analytical electron microscope", Ultramicroscopy 78, 1999, pp. 89-101.

* cited by examiner

Primary Examiner—Maureen M Wallenhorst
(74) Attorney, Agent, or Firm—Squire, Sanders & Dempsey L.L.P.

(57) ABSTRACT

There is provided a method for preparing an analytical standard used for microbeam X-ray fluorescence analysis which includes: a mixing step in which an element is added to a base material, and the base material and the element are mixed by stirring to obtain a mixed solution; a deaeration step in which the mixed solution is deaerated; a freeze step in which the mixed solution is slowly frozen; and a cutting step in which a thin section is cut out from the frozen mixed solution. In order to surely remove bubbles from the mixed solution, the deaeration step may contain a stationary step in which the mixed solution is allowed to stand still at room temperature; or the stationary step includes a removal step in which gas contained in the mixed solution which is allowed to stand still is removed with a suction apparatus.

6 Claims, 4 Drawing Sheets

FIG.2
(a) 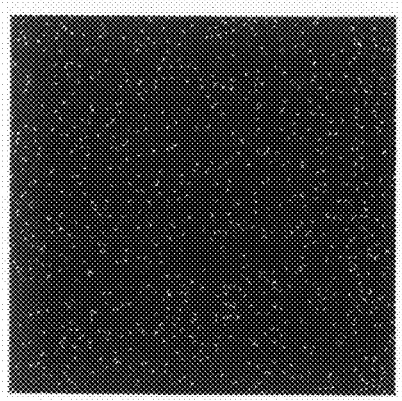  (b) 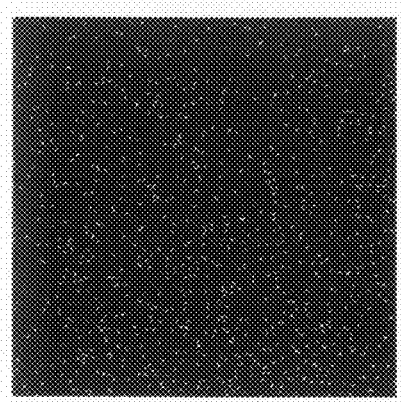
FIG.3
(a) 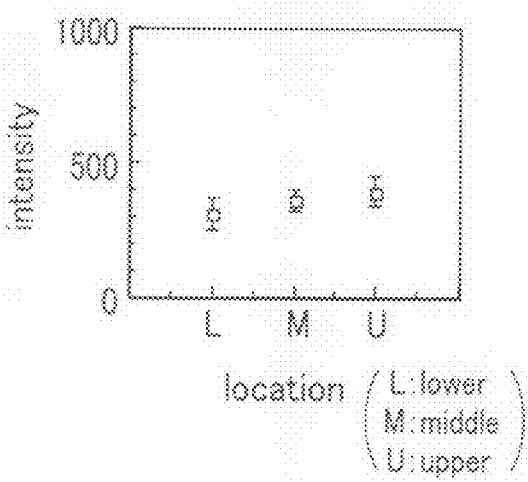  (b) 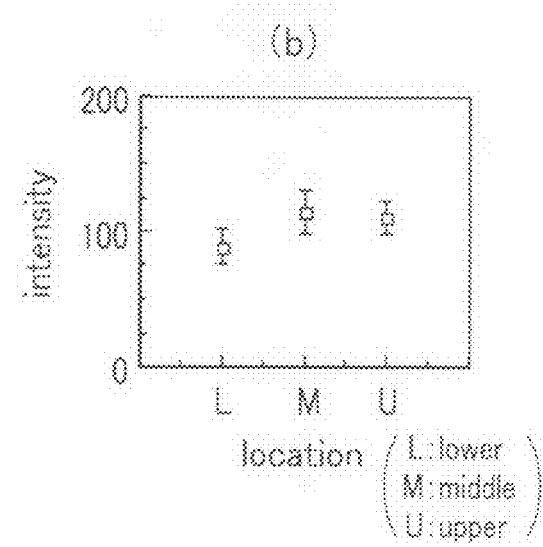

FIG.6
(a) 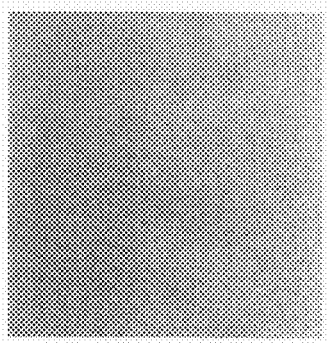
(b) 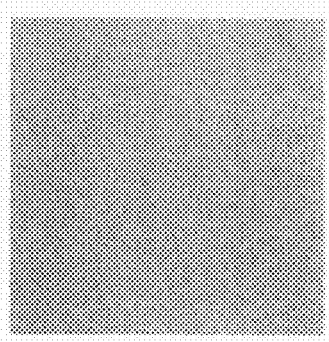
(c) 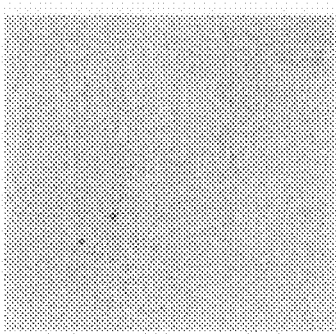
(d) 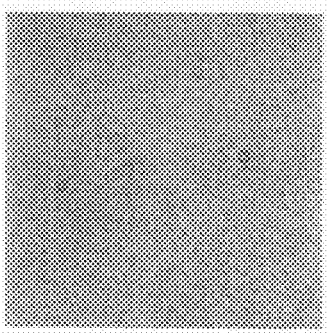
(e) 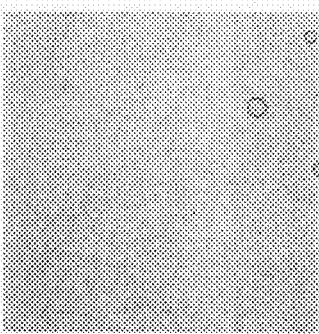
(f) 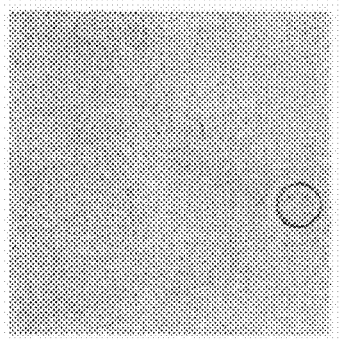
FIG.7
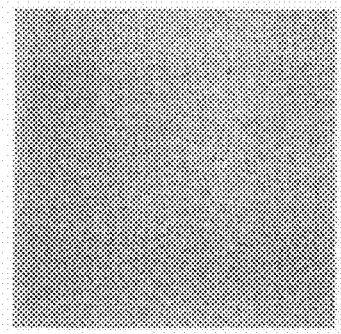

METHOD FOR PREPARING ANALYTICAL STANDARD, AND ANALYTICAL STANDARD PREPARED BY THE SAME

BACKGROUND OF THE INVENTION

1. Field of the Invention

The present invention relates to a method for preparing an analytical standard used for an elemental analysis utilizing microbeam, and an analytical standard prepared by the method.

2. Description of the Related Art

Conventionally, as a technique for a local elemental analysis, there can be mentioned a microbeam X-ray fluorescence analysis in which: a sample is irradiated with sharp excitation light of from a several hundred-nanometer to several-micrometer radius; a type of element is specified based on energy of the generated X-ray fluorescence; and abundance of the element is determined based on the intensity of the generated X-ray fluorescence. The microbeam X-ray fluorescence analyses are classified into several categories depending on the type of the excitation light. Among these, because of less damage on the sample during measurement, attentions have been paid to a synchrotron radiation X-ray fluorescence analysis (SR-XRF) and a proton (particle) induced X-ray emission analysis (PIXE), and they have been widely used. The microbeam X-ray fluorescence analysis has been utilized in various fields, including: a homogeneity test of metal evaporated onto electronic parts (material engineering); an analysis of element localization in mineral samples (earth science); detection of pollutant element in environmental samples, such as suspended particles in the atmosphere (environmental science); and examination of nutritional state by hair analysis or distribution of trace element in tissues (medical science) and the like. In recent years, the detection sensitivity has remarkably improved by the introduction of large facilities for microbeam analysis, and accordingly the utilization of microbeam X-ray fluorescence analysis in the biomedical field has been remarkably boosted.

In the microbeam X-ray fluorescence analysis, an analytical standard (which may be also called "analytical standard sample" or "analytical standard preparation") is used. Herein, the analytical standard means a sample to be used as a standard in a series of measurements for the purpose of measurement accuracy control and quantification. The analytical standard contains an element of a known concentration, and the concentration of the sample of interest can be obtained, for example, from the intensity of the X-ray fluorescence of the sample of interest, by comparing with the intensity of the X-ray fluorescence of the analytical standard at different concentrations as reference. Therefore, it is desirable that the physical properties of the analytical standard be similar to those of the sample to be measured.

For the analytical standard, for example, there has been known a sliced glass containing an element of a known concentration, as well as a standard prepared by evaporating metal onto a thin film (hereinafter, referred to as "analytical standard of evaporation type"), and a disclosure has been made that these analytical standards are applied to the microbeam X-ray fluorescence analysis (see, for example, Non-Patent Document 1). Herein, the expression "evaporating metal" means a treatment in which a metal is vaporized and attached to a surface of a substrate.

Further, for the analytical standard, for example, there has been known an analytical standard obtained by dropping metal solution on a filter paper and drying the filter paper (hereinafter, referred to as "analytical standard by droplet drying method"), and a disclosure has been made that the analytical standard is applied to the microbeam X-ray fluorescence analysis (see, for example, Non-Patent Document 2).

Non-Patent Document 1: M. Watanabe, and D. B. Williams, Atomic-level detection by X-ray microanalysis in the analytical electron microscope, Ultramicroscopy 78 (1999) 89-101

Non-Patent Document 2: K. Watanabe, O. Miyakawa, and M. Kobayashi, New method for quantitative mapping of metallic elements in tissue sections by electron probe microanalyzer with wavelength dispersive spectrometers, Journal of Electron Microscopy 50 (2001) 77-82

The analytical standard of evaporation type disclosed in the Non-Patent Document 1 can be applied to fields, such as material engineering and measurement engineering. However, it is often the case that such an analytical standard cannot be applied to the measurement of biological samples of interest in biomedical field. In other words, the amount of the element present in a biological sample to be measured frequently is as small as several ppm or less, which leads to a large gap in the element content between the biological sample to be measured and the analytical standard of evaporation type. In addition, the biological sample to be measured usually has high transparency to excitation light, which also leads to a notable difference in the transparency to excitation light between the biological sample to be measured and the analytical standard of evaporation type.

Moreover, the analytical standard by droplet drying method disclosed in the above-mentioned Non-Patent Document 2 may not be used as an analytical standard, depending on the types of the element. For example, when mercury is dropped, mercury itself may be vaporized depending on its chemical form. This may result in, in a drying step after dropping, an uneven element distribution at the portion where mercury was dropped. As a result, it becomes difficult to obtain an analytical standard containing mercury of a desired concentration.

Therefore, the object of the present invention is to solve the above-mentioned problems and to provide an analytical standard used for an elemental analysis utilizing microbeam and a method for preparing the analytical standard.

SUMMARY OF THE INVENTION

In order to attain the above-mentioned object, the invention as set forth in Claim 1 is a method for preparing an analytical standard used for microbeam X-ray fluorescence analysis including: a mixing step in which an element is added to a base material and the base material and the element are mixed by stirring to obtain a mixed solution; a deaeration step in which the obtained mixed solution is deaerated; a freeze step in which the deaerated mixed solution is slowly frozen at a cooling rate slower than −4.4° C./min. at which bubbles disappear from the mixed solution when freezing is completed; and a cutting step in which a thin section is cut out from the frozen mixed solution.

According to this method, the mixed solution in which the element is nearly homogeneously dispersed in the base material can be obtained by mixing; gas can be removed from the mixed solution by deaeration; gas can be removed from the mixed solution by slow freeze; and then a thin section can be obtained. With this method, an analytical standard can be obtained in which an element is contained in a trace amount and transparency to excitation light is high, which are the features of the biological sample. Therefore, it becomes possible to apply an elemental analysis utilizing microbeam to biological samples.

The invention as set forth in Claim 2 is the method according to Claim 1 wherein the freeze step includes a stationary step in which the mixed solution is allowed to stand still at room temperature.

According to this method, by allowing the mixed solution to stand still at room temperature before freezing, lowering of the temperature of the mixed solution can be made slower. Therefore, it becomes further possible to surely remove gas from the mixed solution.

The invention as set forth in Claim 3 is the method according to Claim 1 or 2 wherein the stationary step includes a removal step in which gas contained in the mixed solution which is allowed to stand still is removed with a suction apparatus.

According to this method, while the mixed solution is allowed to stand still at room temperature, gas contained in the mixed solution can be removed with the suction apparatus. Therefore, it becomes further possible to surely remove gas contained in the mixed solution.

The invention as set forth in Claim 4 is the method according to any one of Claims 1 to 3, wherein the freeze step is performed at a cooling rate slower than −2.9° C./min.

According to this method, in the freeze step, the mixed solution can be slowly frozen at a cooling rate slower than −2.9° C./min. Therefore, it becomes further possible to surely remove gas contained in the mixed solution.

Further, the invention as set forth in Claim 6 is an analytical standard prepared by the method according to any one of Claims 1 to 3. The invention as set forth in Claim 5 is an analytical standard prepared by the method according to Claim 4.

According to these analytical standards, it becomes possible to provide an analytical standard prepared by the method according to any one of Claims 1 to 4.

According to the present invention, it becomes possible to provide an analytical standard used for an elemental analysis utilizing microbeam, and a method for preparing the analytical standard.

BRIEF DESCRIPTION OF THE DRAWINGS

FIG. 2 shows elemental images of the analytical standard prepared by the method according to the embodiment in which: FIG. 2(a) shows a case where the element is zinc; and FIG. 2(b) shows a case where the element is selenium.

FIG. 3 shows homogeneity of the frozen blocks of the analytical standards prepared by the method according to the embodiment in which: FIG. 3(a) shows a case where the element is selenium; and FIG. 3(b) shows a case where the element is mercury.

FIG. 4 shows calibration curves of the analytical standard prepared by the method according to the embodiment in which: FIG. 4(a) shows a case where the element is selenium; FIG. 4(b) shows a case where the element is zinc; and FIG. 4(c) shows a case where the element is mercury.

FIG. 6 shows analytical standards prepared by either the method according to the embodiment or other methods in which: FIG. 6(a) shows a case where the analytical standard was prepared by the method according to the embodiment described above; FIGS. 6(b)-(e) show a case where the cooling-down period of the analytical standard was altered; and FIG. 6(f) shows a state in a case where the analytical standard was not allowed to stand still at room temperature.

FIG. 7 is an analytical standard prepared by performing deaeration with an aspirator in a stationary step of the method for preparing analytical standard according to the embodiment.

DETAILED DESCRIPTION OF THE EXEMPLARY EMBODIMENTS

Embodiments of the present invention will be described below with reference to the drawings.

Figure 1:
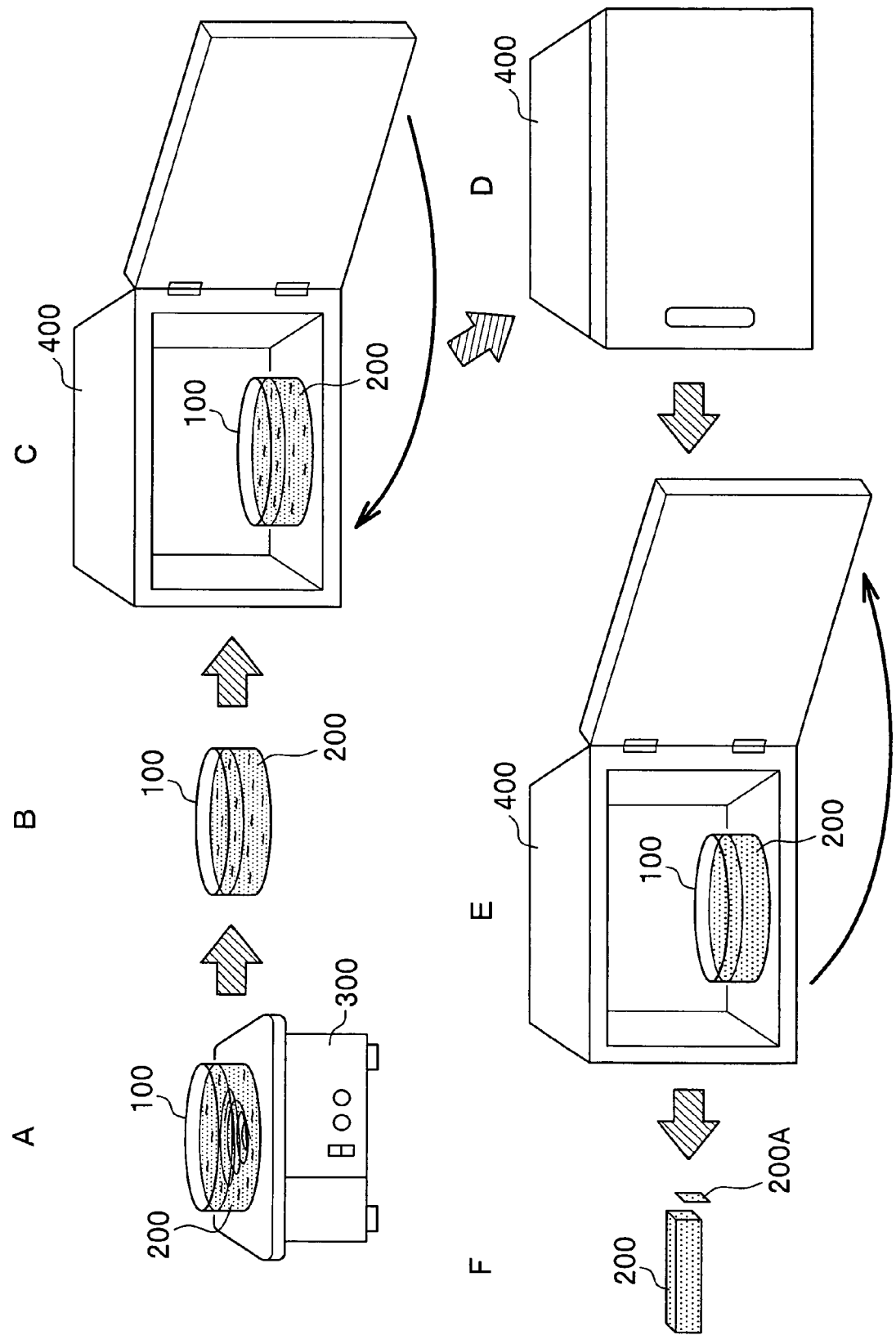
FIG. 1 is a diagram illustrating a method for preparing an analytical standard according to an embodiment.

FIG. 1 is a diagram illustrating a method for preparing an analytical standard according to the present embodiment. The method for preparing an analytical standard used for microbeam X-ray fluorescence analysis in the present embodiment includes a mixing step A in which an element is added to a base material and the base material and the element are mixed by stirring to obtain a mixed solution; a deaeration step B in which the mixed solution is deaerated; a freeze step D in which the mixed solution is slowly frozen; and a cutting step F in which a thin section is cut out from the frozen mixed solution.

As shown in FIG. 1, first, an arbitrary amount of an element is added to a base material to thereby prepare a reference material 200, and the mixture is mixed in a container 100 (mixing step A). For the base material, it is preferable to use a material which is sliceable as a solid state into sections of a thickness of approximately 5-40 µm (e.g. a liquid having a high viscosity at room temperature), and specifically, OTC compound (4.26% of polyethylene glycol; 10.24% of polyvinyl alcohol; and 85.5% of buffering component-containing water) is preferable which is used as a base during preparation of a frozen section. For example, a solution mainly composed of polyvinyl alcohol, such as Arabic YAMATO liquid glue (manufactured by YAMATO Co., Ltd.) may be used as a base, since the material itself is less contaminated with elements. In addition, for example, a solution mainly composed of acrylic resin, such as Acrytron (manufactured by Mitsubishi Rayon Co., Ltd.) may be used as a base. Examples of the element to be added include metal elements, such as zinc, selenium, mercury and tin. It is preferable that the element is added to the base material so that the concentration of the element in the reference material 200 becomes approximately 1-500 ppm. The addition of the element to the base material can be performed simply by adding an aqueous solution containing the element dissolved therein to the base material, for example. It is further preferable that, during mixing, a stirrer bar (not shown) is put in the reference material 200 and the mixing is conducted by gently stirring with a stirrer 300.

Next, the reference material (mixed solution) 200 is deaerated (deaeration step B). It is preferable that the deaeration step B includes a stationary step in which the reference material 200 is allowed to stand still at room temperature. The room temperature is not specifically limited, and it may be as low as, for example, 4° C., as long as the reference material 200 is maintained not frozen. The time period for allowing the reference material 200 to stand still at room temperature is preferably 5 minutes or more in the case of the room temperature of approximately 25° C., and it should be made longer at lower temperatures. It is often the case that gas (such as bubbles and dissolved gas) is contained in the reference material 200 after the mixing step A, and if the reference material 200 is used as-is as an analytical standard, it is extremely difficult to accurately measure the energy and intensity of X-ray fluorescence generated by application of excitation light to the reference material 200. Therefore, in order to remove gas contained in the reference material 200, deaeration is performed during the deaeration step B and the slow freeze step D, which will be described below. Moreover, during the stationary step B, deaeration process on the reference material 200 may be accelerated by a suction apparatus, such as an aspirator. Herein, the expression "slow freezing (slowly frozen)" means a freezing at a cooling rate at which bubbles disappear when freezing is completed, as will be described below.

Next, the container 100 containing the reference material 200 is placed in a freezer 400 (introduction step C), where the reference material 200 is slowly frozen (freeze step D). In order to make the freezing slow, it is preferable that the cooling rate is set slower than −2.9° C./min. The cooling rate may be slower than −4.4° C./min. With this freeze step D, the reference material 200 can be made in a solid state (sherbet-like state), from which a thin section can be prepared. In addition, with this freeze step D, another effect of removing gas from the reference material 200 can be obtained, as described above. After the freezing of the reference material 200 is completed, the container 100 containing the frozen reference material 200 is taken out from the freezer 400 (take-out step E).

From the reference material 200 obtained through the above-mentioned steps, a thin section 200A is cut out and dried as a section standard, to thereby obtain an analytical standard (not shown) (cutting step F). In the cutting step F, the thin section 200A may be cut out from the reference material 200 using, for example, a cryostat type CM1510 (manufactured by Leica Microsystems AG). The cryostat type CM1510 (manufactured by Leica Microsystems AG) includes a box with a cooling system and a microtome disposed therein which is configured to slice specimens by sliding a special knife over the specimen and is operatable at −20° C. Also in the cutting step F, it is preferable that a frozen block is immediately placed on a specimen stage at room temperature, and the thin section 200A be cut out in the cryostat again at −20° C. That is, it is preferable that the period for operating at room temperature is made short, such as approximately 10 seconds, to thereby keep the temperature of the specimen at −20° C. or around −20° C. as a whole. It is preferable that the thickness of the thin section 200A is approximately 5-40 μm.

According to the method for preparing an analytical standard as described above, it becomes possible to adjust the element content of the obtained analytical standard to the same level as the element content (several ppm or less) of the biological sample. In addition, for the transparency to excitation light, it becomes possible to adjust the transparency of the obtained analytical standard to the same level as the transparency of the biological sample. Accordingly, with the use of the analytical standard obtained through the steps described above, the elemental analysis using microbeam can be applied to biological samples.

EXAMPLES

Next, Examples with which the effects of the present invention are demonstrated will be described below.

Example 1

FIG. 2 shows elemental images of the analytical standard prepared by the method according to the embodiment described above in which: FIG. 2(*a*) shows a case where the element is zinc; and FIG. 2(*b*) shows a case where the element is selenium.

In an example illustrated in FIG. 2, 1.98 g of OTC compound was charged in a container (in a shape of an ellipsoid with a major axis of 27 mm, a minor axis of 22 mm and a depth of 4 mm) and 20 μl of an element solution (in the case of FIG. 2(*a*), a zinc chloride solution prepared by dissolving zinc chloride in distilled water to a concentration of 50,000 ppm in terms of zinc; and in the case of FIG. 2(*b*), a sodium selenite solution prepared by dissolving sodium selenite in distilled water to a concentration of 50,000 ppm in terms of selenium) was added to a final concentration of 500 ppm in terms of zinc in the OTC compound. A stirring bar (with a length of 15 mm and a diameter of 2 mm) was put in the container. The mixture was stirred with a magnetic stirrer for 5 minutes, allowed to stand still at room temperature (approximately 25° C.) for 5 minutes, and then frozen in a freezer at −20° C. Approximately 10 minutes after the introduction into the freezer, the mixture began to turn into a white solid. After the freezing is completed, a very surface portion of approximately 400 μm-thickness was removed, and a section having a thickness of 20 μm was prepared. The section was attached to a polypropylene thin film and left at room temperature to be allowed to dry, to thereby obtain an analytical standard. An area of 500× 500 μm$^2$ Of the section standard was scanned with nanobeam using a micro PIXE analytical system (OM2000 manufactured by Oxford Microbeams Ltd.) (a beam diameter of 0.4 μm×0.65 μm and an integrated current of 0.25-0.3 μC). A dot represents a presence of the element. It can be seen from the scan that zinc (see FIG. 2(*a*)) and selenium (see FIG. 2(*b*)) added to the OTC compound are almost evenly distributed.

Example 2

FIG. 3 shows graphs of element distribution in a depth direction in the frozen block of the analytical standard prepared by the method according to the embodiment described above in which; FIG. 3(*a*) shows a case where the element is selenium; and FIG. 3(*b*) shows a case where the element is mercury.

In the general microbeam X-ray fluorescence analysis, due to the limitation in the detector property, a subject to be measured is X-ray fluorescence which is detectable in the energy region of approximately 1-20 keV. Therefore, in a case of the element with which X-ray fluorescence as K-line (main peak) is out of the above-mentioned energy region, the detection should be made with L-line or M-line, detection efficiency of which is lower than that of K-line. As a representative element having such a property, mercury was selected, and a comparison was made with selenium detectable with K-line. Mercury is one of the elements with which it is difficult to obtain excellent results when the analytical standard by droplet drying method (see the above-mentioned Non-Patent Document 2) is used, since the analytical standard may be vaporized during drying.

In an example illustrated in FIG. 3, an element solution (in the case of FIG. 3(*a*), a sodium selenite solution at a concentration of 50,000 ppm in terms of selenium and in the case of FIG. 3(*b*), a mercuric chloride solution at a concentration of 50,000 ppm in terms of mercury) was used. Other conditions are substantially the same as those in Example 1. After the freezing is completed, a sliced section was prepared from the resultant solid block of approximately 2.4 cm$^2$, which sliced section was taken as an analytical standard. Homogeneity of the block was examined using a micro PIXE analytical system (OM2000 manufactured by Oxford Microbeams Ltd.). Specifically, section standards (thickness: 20 μm) were prepared from a lower portion (L), a middle portion (M) and an upper portion (U) (except the very surface portion) of the block, and for each sample, 3 areas of 500×500 µm² were scanned with nanobeam (a beam diameter of 0.4 µm×0.65 µm) (an integrated current of 0.24 µC), and a mean value and standard deviation of the resultant intensity were plotted. As is apparent from the graphs, an analytical standard exhibits highly similar results in the distribution of selenium (see FIG. 3(a)) and mercury (see FIG. 3(b)) added to the OTC compound, regardless of the location in the block from which the thin section was cut out. For mercury, though the detection efficiency would otherwise be poorer than that of selenium since the detection should be made with L-line, an excellent result was obtained with the analytical standard prepared by the method according to the embodiment described above, which demonstrates the validity of the present invention.

Example 3

Figure 4:
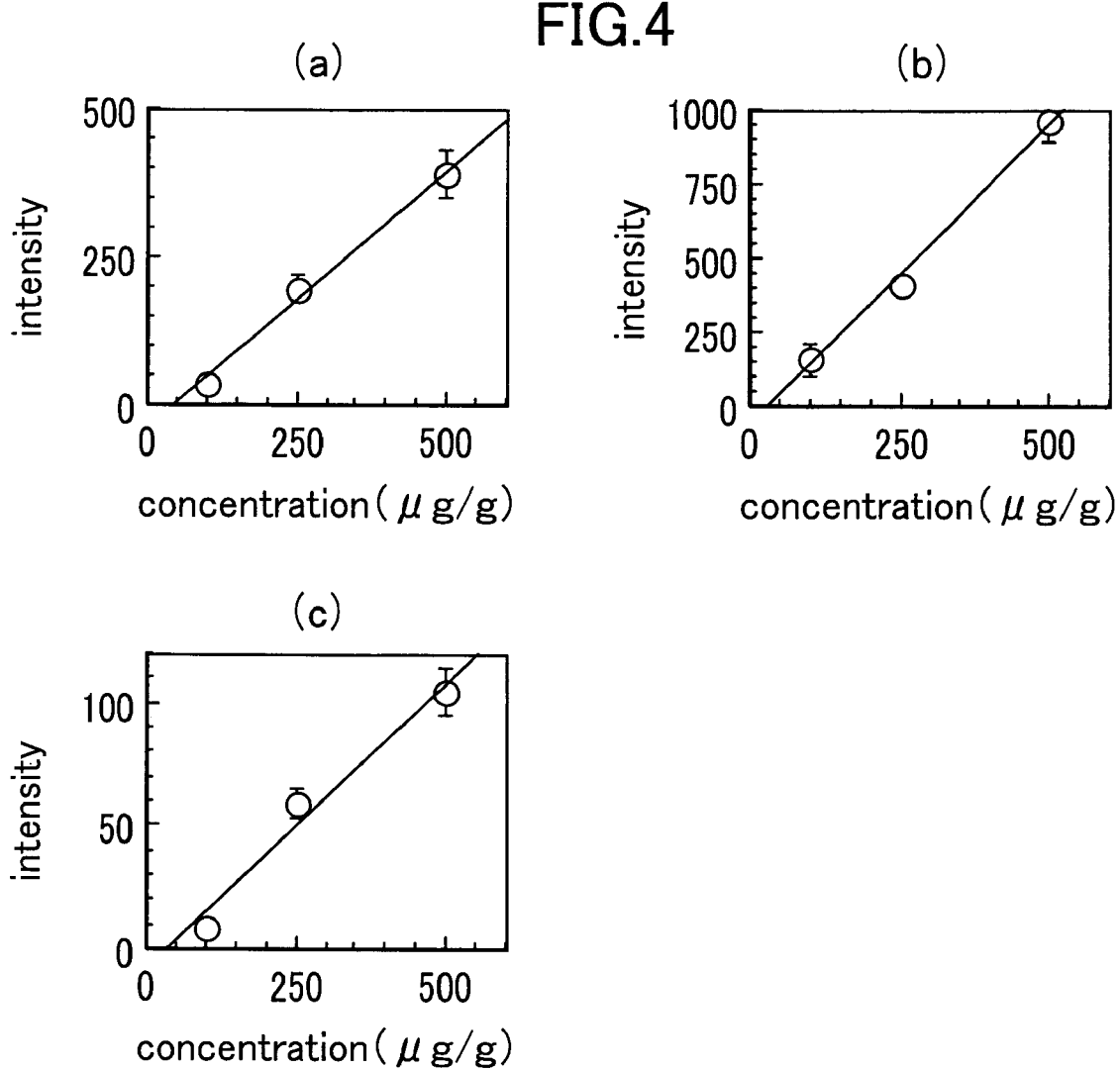

FIG. 4 shows calibration curves of the analytical standard prepared by the method according to the embodiment described above in which: FIG. 4(a) shows a case where the element is selenium; FIG. 4(b) shows a case where the element is zinc; and FIG. 4(c) shows a case where the element is mercury.

In an example illustrated in FIG. 4, an element solution (in the case of FIG. 4(a), a sodium selenite solution, in the case of FIG. 4(b), a zinc chloride solution, and in the case of FIG. 4(c), a mercuric chloride solution) was added to the OTC compound to the final concentrations of 100, 250 and 500 ppm. Other conditions are substantially the same as those in Example 1. For each sample, 3 areas of 500×500 µm² were scanned with nanobeam (an integrated current of 0.24 µC) using substantially the same analyzer as that of Example 2, and a mean value and standard deviation of the resultant intensity were plotted, to thereby obtain a calibration curve. It was found that, with respect to all of selenium, zinc and mercury, the calibration curve was nearly linear.

Example 4

Figure 5:
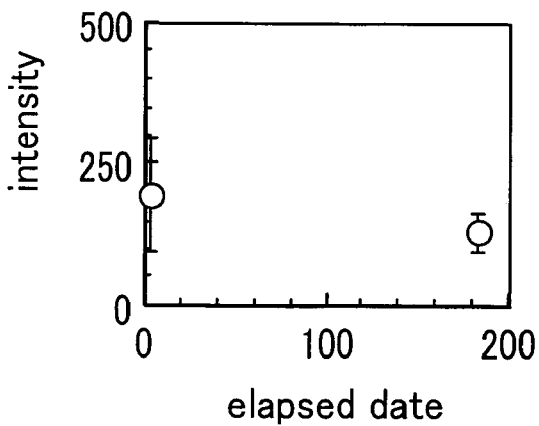
FIG. 5 is a graph showing stability over time of the analytical standard prepared by the method according to the embodiment.

FIG. 5 is a graph showing stability over time of the analytical standard prepared by the method according to the embodiment described above.

In an example illustrated in FIG. 5, an analytical standard at a concentration of 500 ppm in terms of mercury was prepared in substantially the same manner as in Example 3. The analytical standard was maintained in a special container and reserved in a dust proof box. For each of the analytical standards with different elapsed dates (4 days and 184 days (approximately 6 months) after the preparation), 3 areas of 500× 500 µm² were scanned with nanobeam (beam diameter of 0.4 µm×0.65 µm) (an integrated current of 0.24 µC) using substantially the same analyzer as that of Example 2, and a mean value and standard deviation of the resultant intensity were plotted. Though mercury to be used in the analytical standard by droplet drying method or the like has been deemed to be unstable, it was demonstrated that the analytical standard by the present method is stable 6 months later.

Example 5

FIG. 6 shows images illustrating states of analytical standards prepared by either the method according to the embodiment described above or other methods in which: FIG. 6(a) shows a case where the analytical standard was prepared by the method according to the embodiment (cooling-down period of 15 minutes); FIGS. 6(b)-(e) show a case where the cooling-down period of the analytical standard was altered (cooling-down periods of 10 minutes for (b), 3 minutes for (c), 2 minutes for (d) and 30 seconds for (e)); and FIG. 6(f) shows a state in a case where the analytical standard was not allowed to stand still at room temperature.

In an example illustrated in FIG. 6(a), in substantially the same manner as in Example 1, to the OTC compound was added a 1/100 amount of distilled water (this process corresponds to the addition of the element solution). The mixture was stirred for 5 minutes and allowed to stand still for 5 minutes. Subsequently, the mixture was frozen in a freezer at −20° C. for 15 minutes. In examples illustrated in FIGS. 6(b)-(e), liquid nitrogen, dry ice or the like was used and only the cooling-down period was altered as compared with the case of FIG. 6(a). Specifically, the cooling-down periods are 10 minutes for (b), 3 minutes for (c), 2 minutes for (d) and 30 seconds for (e). In an example illustrated in FIG. 6(f), the analytical standard of the same concentration as above was stirred for 5 minutes, and immediately frozen in a freezer at −20° C., without being allowed to stand still at room temperature. FIGS. 6(a)-(f) show images of analytical standards (thickness of 20 µm) obtained by these various conditions. Referring to FIG. 6(a), with the use of the method for preparing an analytical standard according to the above-mentioned embodiment, no bubbles are contained in the analytical standard. On the other hand, referring to FIGS. 6(b)-(d), bubbles are contained in the analytical standard due to rapid freezing. Based on the image of FIG. 6(b), it is determined that there is a boundary at this cooling-down period for quality retention of the analytical standard. Specifically, in the case of FIG. 6(b), the mixture was cooled from room temperature (24° C.) to the freezer temperature (−20° C.) in 10 minutes, i.e., at the cooling rate of (−20° C.-24° C.)/10 minutes=−4.4° C./min; and in the case of FIG. 6(a), the mixture was cooled from room temperature (24° C.) to the freezer temperature (−20° C.) in 15 minutes, i.e., at the cooling rate of (−20° C.-24° C.)/15 minutes=−2.9° C./min. Accordingly, it is preferable that at least the cooling rate is slower than −4.4° C./min, and it is more preferable that the cooling rate is slower than −2.9° C./min. Referring to FIG. 6(c), it is apparent that bubbles are contained in the analytical standard since the mixture was immediately frozen without being allowed to stand still at room temperature.

Example 6

FIG. 7 is an image showing a state of an analytical standard prepared by performing deaeration with an aspirator in a stationary step of the method for preparing analytical standard according to the embodiment described above.

In an example illustrated in FIG. 7, a mixture was stirred for 5 minutes, and immediately after the stirring, deaeration was performed for 25 minutes using an aspirator while allowing the mixture to stand still at room temperature, and the mixture was frozen in a freezer at −20° C. for 15 minutes. An image of the analytical standard (thickness of 20 µm) obtained with this method is shown in FIG. 7. No bubbles are seen, indicating an excellent state.

What is claimed is:

1. A method for preparing an analytical standard used for microbeam X-ray fluorescence analysis comprising:
   a mixing step in which an element is added to a base material and the base material and the element are mixed by stirring to obtain a mixed solution;
   a deaeration step in which the obtained mixed solution is deaerated;
   a freeze step in which the deaerated mixed solution is slowly frozen at a cooling rate slower than −4.4° C./min.

at which bubbles disappear from the mixed solution when freezing is completed; and a cutting step in which a thin section is cut out from the frozen mixed solution.

2. The method for preparing an analytical standard according to claim 1, wherein the deaeration step comprises a stationary step in which the mixed solution is allowed to stand still at room temperature.

3. The method for preparing an analytical standard according to claim 2, wherein the stationary step comprises a removal step in which gas contained in the mixed solution which is allowed to stand still is removed with a suction apparatus.

4. The method for preparing an analytical standard according to claim 1, wherein the freeze step is performed at a cooling rate slower than $-2.9°$ C./min.

5. An analytical standard prepared by the method according to claim 4, wherein the analytical standard does not include bubbles.

6. An analytical standard prepared by the method according to claim 1, wherein the analytical standard does not include bubbles.

* * * * *